United States Patent [19]

Vernon et al.

[11] Patent Number: 5,034,551
[45] Date of Patent: Jul. 23, 1991

[54] PROCESS FOR RECOVERY OF ORGANOTIN ESTERS FROM REACTION MIXTURES CONTAINING THE SAME AND RE-USE OF THE RECOVERED ORGANOTIN COMPOUNDS

[75] Inventors: Nicholas M. Vernon, Athens; Robert E. Walkup, Watkinsville, both of Ga.

[73] Assignee: Noramco, Inc., Athens, Ga.

[21] Appl. No.: 512,690

[22] Filed: Apr. 23, 1990

[51] Int. Cl.$^5$ .............................................. C07H 7/22
[52] U.S. Cl. ...................................... 556/89; 556/88; 536/119
[58] Field of Search .................. 556/89, 83, 87, 88; 536/119, 120, 121, 122, 124

[56] References Cited

U.S. PATENT DOCUMENTS

| | | | |
|---|---|---|---|
| 3,846,459 | 11/1974 | Stapfer | 556/89 |
| 3,962,295 | 6/1976 | Collins et al. | 556/91 |
| 4,254,017 | 3/1981 | Dworkin et al. | 556/89 X |
| 4,434,102 | 2/1984 | Spiegelman et al. | 556/89 X |
| 4,711,920 | 12/1987 | Kugele et al. | 556/91 X |
| 4,950,746 | 8/1990 | Navia | 536/119 |

Primary Examiner—Arthur C. Prescott
Attorney, Agent, or Firm—Charles J. Metz

[57] ABSTRACT

A process which comprises extracting 1,3-diacyloxy-1,1,3,3-tetra(hydrocarbyl) distannoxane from a mixture containing 1,3-diacyloxy-1,1,3,3-tetra(hydrocarbyl)distannoxane, a sucrose-6-ester, and polar aprotic solvent, which process comprises the steps of:

(a) contacting said mixture, in the presence of a small amount of water, with an organic solvent that is substantially immiscible with water to form thereby an extraction mixture, wherein the amount of water employed is sufficient to cause efficient partitioning of said 1,3-diacyloxy-1,1,3,3-tetra(hydrocarbyl)distannoxane from a first phase comprising said polar aprotic solvent into second phase comprising said organic solvent;

(b) agitating the extraction mixture for a period of time and at a temperature sufficient to form thereby a two-phase mixture wherein the preponderance of the 1,3-diacyloxy-1,1,3,3-tetra(hydrocabyl)distannoxane in the extraction mixture is contained in said second phase and essentially all of the sucrose-6-ester in the extraction mixture is contained in said first phase; and (c) separating said first phase from said second phase.

30 Claims, No Drawings

PROCESS FOR RECOVERY OF ORGANOTIN ESTERS FROM REACTION MIXTURES CONTAINING THE SAME AND RE-USE OF THE RECOVERED ORGANOTIN COMPOUNDS

The invention relates to a process for the recovery of distannoxane diesters from reaction mixtures containing the same, and in a preferred embodiment, the recovered distannoxane diester is recycled for further reaction.

BACKGROUND OF THE INVENTION

The sucrose molecule contains three primary hydroxyl groups and five secondary hydroxyl groups. Therefore, when it is desired to prepare derivatives of sucrose involving reaction of the hydroxyl groups, it can be a major synthesis problem to direct the reaction only to the desired hydroxyl groups. For instance, the artificial sweetener 4,1',6'-trichloro-4,1',6'-trideoxygalacto-sucrose ("sucralose") is derived from sucrose by replacing the hydroxyls in the 4, 1', and 6' positions with chlorine. (In the process of making the sweetener, the stereo configuration at the 4 position is reversed - hence the compound is a galactosucrose.) This compound and methods for synthesizing it are disclosed in U.S. Pat. Nos. 4,343,934, 4,362,869, 4,380,476 and 4,435,440. The direction of the chlorine atoms to only the desired positions is a major synthesis problem, especially since the hydroxyls that are replaced are of differing reactivity (two are primary and one is secondary; the synthesis is further complicated by the fact that the primary hydroxyl in the 6 position is unsubstituted in the final product). The preparation of this sweetener is only one illustration of the synthesis of sucrose derivatives wherein it is desired either to derivatize certain specific hydroxyl groups, and only such hydroxyl groups, or to derivatize only a specified number of the hydroxyls, perhaps in this latter case without particular regard to which particular hydroxyl(s) are derivatized. The preparation of sucrose-based monoester surfactants is a commercial example of monosubstitution on the sucrose molecule.

Some of the Applicants herein and their colleagues at Noramco, the assignee of this application, have developed useful processes for sucrose-6-ester production utilizing as intermediates certain tin compounds. For instance, the distannoxane-based preparation of sucrose-6-esters was described in Navia, PROCESS FOR SYNTHESIZING SUCROSE DERIVATIVES BY REGIOSELECTIVE REACTION, U.S. patent application Ser. No. 220,641, filed on July 18, 1988 now U.S. Pat. No. 4,950,746, and assigned to the same assignee as this application. Navia disclosed that a suitable di(hydrocarbyl)tin-based species, such as dibutyltin oxide, dioctyltin oxide, dibutyltin dimethoxide, or the like, could be combined with a hydroxyl group-containing compound such as a monohydric alcohol or a simple phenol in such a way as to produce a reactive distannoxane intermediate [i.e., a 1,3-di(hydrocarbyloxy)-1,1,3,3-tetra(hydrocarbyl)distannoxane], which could then be reacted with sucrose to afford a 1,3-di-(6-O-sucrose)-1,1,3,3-tetra(hydrocarbyl)distannoxane. Navia also described the ready preparation of sucrose-6-esters by the treatment of these organotin-sucrose adducts with a suitable acylating agent in an appropriate solvent or solvent mixture.

Another tin-mediated process for producing sucrose-6-esters is described in copending U.S. patent application Ser. No. 512,692, SUCROSE-6-ESTER PRODUCTION PROCESS, filed on the same day as this application by D. S. Neiditch, N. M. Vernon, and R. E. Wingard. The process described by Neiditch et al. comprises reacting sucrose with a di(hydrocarbyl)tin oxide in an inert organic vehicle for a period of time and at a temperature sufficient to produce a 1,3-di-(6-O-sucrose)-1,1,3,3-tetra(hydrocarbyl)distannoxane. In a preferred aspect of the process of Neiditch et al., the 1,3-di-(6-O-sucrose)-1,1,3,3-tetra(hydrocarbyl)distannoxane thus produced is reacted with an acylating agent at a temperature and for a period of time sufficient to produce a sucrose-6-ester.

A further tin-mediated process for the production of sucrose-6-esters is described in U.S. patent application Ser. No. 499,731, for SELECTIVE 6-ACYLATION OF SUCROSE MEDIATED BY CYCLIC ADDUCTS OF DIALKYLTIN OXIDES AND DIOLS, filed by R. E. Walkup, N. M. Vernon, and R. E. Wingard on Mar. 23, 1990, and assigned to the same assignee as this application. The process described by Walkup et al. comprises the steps of:

(a) reacting a di(hydrocarbyl)tin oxide, such as a dialkyltin oxide, with a dihydric alcohol, alkanolamine, or an enolizable α-hydroxy ketone (i.e., an α-hydroxy ketone that is capable of enolization to an enediol) in an inert organic reaction vehicle with removal of water by azeotropic distillation and at a temperature and for a period of time sufficient to produce a cyclic adduct of said diaklytin oxide and said dihydric alcohol, alkanolamine, or enolizable α-hydroxy ketone;

(b) reacting said cyclic adduct product of Step (a) with sucrose in an inert organic reaction vehicle in which sucrose has an appropriate degree of solubility, such as a dipolar aprotic liquid, at a temperature and for a period of time sufficient to produce a 6-O-[dihydrocarbyl(hydroxy- or amino- or oxohydrocarbyl)stannoxyl]sucrose; and (c) reacting the product of Step (b) with an acylating agent to produce a sucrose-6-ester.

In the Navia process, the Walkup et al. process, and the Neiditch et al. process, the reaction mixture containing the sucrose-6-ester ("S-6-E") also contains as a by-product a 1,3-diacyloxy-1,1,3,3-tetra(hydrocarbyl)distannoxane or distannoxane diester ("DSDE"). This invention provides a process for recovering the said DSDE and, preferably, recycling the tin compound for further production of S-6-E.

BRIEF SUMMARY OF THE INVENTION

The invention provides a process which comprises extracting a DSDE from a mixture containing a DSDE, a sucrose-6-ester, and a polar aprotic solvent, which process comprises the steps of:

(a) contacting said mixture, in the presence of a small amount of water, with an organic solvent that is substantially immiscible with water to form thereby an extraction mixture, wherein the amount of water employed is sufficient to cause efficient partitioning of said DSDE from a first phase comprising said polar aprotic solvent into a second phase comprising said organic solvent;

(b) agitating the extraction mixture for a period of time and at a temperature sufficient to form a two-phase mixture wherein the preponderance of the DSDE contained in the extraction mixture is contained in said second phase and essentially all of the S-6-E contained in the extraction mixture is contained in said first phase; and (c) separating said first phase from said second phase.

The presence of a small amount of water in the extraction mixture serves to enable or to significantly enhance the partitioning of the DSDE into said organic solvent while the S-6-E remains dissolved in the polar aprotic solvent, so that the DSDE can be extracted almost quantitatively by the said organic solvent while the sucrose-6-ester remains in solution in the polar aprotic solvent.

THE PRIOR ART

The organotin-mediated regioselective 6-position acylations of sucrose to produce sucrose-6-esters are described in the Navia, the Walkup et al., and the Neiditch et al. patent applications described above. The utility of sucrose-6-esters in a process for producing the artificial sweetener 4,1',6'-trichloro-4,1',6'-trideoxygalactosucrose is described, for example, in U.S. application Ser. No. 382,147, for IMPROVED SUCROSE-6-ESTER CHLORINATION, filed July 18, 1989, by R. E. Walkup, N. M. Vernon, and J. L. Navia, and assigned to the same assignee as this application. To the best of Applicants' knowledge, the partitioning of the DSDE byproduct, resulting in situ after sucrose acylation, between two organic solvent phases, said partitioning being promoted by the addition of a small amount of water, has no literature precedent.

DETAILED DESCRIPTION OF THE INVENTION

The invention comprises a process for extracting a distannoxane diester from a mixture containing the same along with a sucrose-6-ester and a polar aprotic solvent, by contacting said mixture with an organic solvent that is substantially immiscible with water and in which the DSDE is soluble, in the presence of a small amount of water. The mixture containing the DSDE, S-6-E, and polar aprotic solvent can be produced by any of the processes described in the above-cited Navia, Neiditch et al., and Walkup et al. patent applications. An understanding of these three processes is useful in order to appreciate the nature of the reaction mixture employed in the process of this invention. Accordingly, these three processes are described in some detail following the Examples that illustrate the process of this invention.

As is indicated above, the process of this invention employs as a starting mixture the product of a process wherein a sucrose-tin adduct is selectively acylated with an appropriate acylating agent (e.g., an acid anhydride), in a polar aprotic medium such as N,N-dimethylformamide (DMF), dimethyl sulfoxide (DMSO), N-methylpyrrolidinone (NMP), N,N-dimethylacetamide (DMA), hexamethylphosphoramide (HMPA), and other polar, aprotic solvents in which sucrose is soluble (the preferred polar aprotic solvent is DMF), to generate a sucrose-6-ester and an acylated form of the tin reagent which possesses substantial solubility in common organic solvents. In accordance with this invention, the organotin byproduct (DSDE) thus derived is separated from the sucrose-6-ester reaction medium by treatment with a small amount of water followed by extraction with an appropriate organic solvent.

The effectiveness of this extraction is significantly and substantially augmented by the addition of a small amount of water to the reaction medium prior to extraction. The extractive tin removal is extraordinarily efficient (>99% extractable organotin removal under optimal conditions with as few as two batch extractions). The raffinate (i.e., the liquid remaining after the tin compound has been extracted) resulting from the extractive tin removal contains the polar aprotic solvent, acylated sucrose derivatives (predominantly the S-6-E), residual water, and residual extractant resulting from cross-solubility. Removal of the water (which must be done when the sucrose-6-ester is to be chlorinated to a sucralose-6-ester) and residual volatiles by distillative methods results in a solution of the acylated sucrose in a polar aprotic solvent.

When the polar aprotic solvent employed is DMF, these distillation bottoms are suitable for direct use in the chlorination reaction described in U.S. patent application Ser. No. 382,147, referred to above, without further treatment or isolation of the sucrose-6-ester. (In the case where the S-6-E was prepared by the method of Walkup et al., removal of the esterified diol, aminoalcohol, or enol, may be conducted prior to chlorination.) The primary product of the chlorination reaction is a sucralose-6-ester, which, upon hydrolysis to remove the acyl group, affords the high-intensity sweetening agent sucralose.

Thus, the invention provides an extractive technique to preferentially and efficiently separate the organotin byproduct resulting from the tin-mediated 6-acylation reactions of sucrose from the acylated carbohydrate derivatives, thereby permitting the crude in situ carbohydrate product of this reaction to be utilized directly in a subsequent chlorination step without resorting to isolation of the intermediate S-6-E. The fact that the separation can be affected with only small amounts of water being added is an important feature of the invention, since the water must be removed from the sucrose-6-ester solution prior to further processing to produce sucralose, and the cost of the removal of this water is proportional to the amount of it present. The DSDE resulting from the separation process of the invention can be recycled into the sucralose reaction sequence by removal of the extraction solvent and either treatment with an equivalent amount of an alkoxide to generate a reactive distannoxane dialkoxide (for reuse in the process of Navia), or reaction with a slight excess of aqueous caustic to regenerate a di(hydrocarbyl)tin oxide (for reuse in any of the three sucrose-6-ester production processes cited above).

By avoiding the isolation of solid product, an overall yield increase for the sucrose-6-ester (as prepared by the processes cited above) can be realized; e.g., 90–93% yield for sucrose-6-benzoate ("S-6-B") and 88–91% yield for sucrose-6-acetate ("S-6-A") by this method, as opposed to yields of approximately 80% for solid S-6-B and 65% for solid S-6-A when crystallization is employed for product isolation. Added benefits include a reduction in the number of solvents employed (e.g., for crystallization wherein acetone or methanol are used), elimination of the need to recycle crystallization mother liquors, elimination of the need to evaporate a polar aprotic solvent such as DMF, and a reduction in the overall number of equipment items required in the process (e.g., isolation and drying equipment for the S-6-E).

Solvents useful in carrying out the extractive removal of the DSDE include aliphatic and aromatic hydrocarbons, ethers, chlorinated hydrocarbons, ketones, and esters which show low cross-solubility with water. (By "low cross-solubility with water" is meant that the extraction solvent dissolves less than about one weight per cent water, and water dissolves less than about one weight per cent of the extraction solvent, both solubilities being determined at temperatures below about 20° C.) Though these solvents are often miscible with DMF or other polar aprotic solvents, the presence of the sucrose-6-ester promotes the separation of the extraction mixture into two phases, while the addition of a small amount of water causes efficient DSDE partitioning, thereby allowing the extraction to proceed. Solvents which may be used include hexane, cyclohexane, heptane, and other aliphatic hydrocarbons; benzene, toluene, xylenes, cumene, and other aromatic hydrocarbons; diethyl, methyl t-butyl, diisopropyl, and other ethers; dichloromethane, chloroform, carbon tetrachloride, di-, tri-, and tetrachlorinated ethanes, polychlorinated aliphatic and aromatic hydrocarbons, chlorobenzene, and other chlorinated hydrocarbons; methyl isobutyl ketone and other water immiscible ketones; and water immiscible ester such as methyl benzoate, isopropyl acetate, and ethyl valerate. The preferred solvents are the least polar; the aliphatic hydrocarbons are preferred as they exhibit lower cross solubility with DMF. To aid the distillative removal of the solvent, a boiling point at atmospheric pressure in the range 60°-100° C. is preferred; most preferred are solvents boiling at about 75°-85° C. at atmospheric pressure.

The extraction solvent is used in an amount sufficient to effectively extract the DSDE present, e.g., in an amount of at least about 1 ml of extraction solvent per gram of DSDE, preferably at least about 1.5 ml of extraction solvent per gram of DSDE, and more preferably at least about 2 ml of extraction solvent per gram of DSDE present in the extraction mixture. The foregoing proportions are appropriate for the first extraction step. In actual practice, two or three extraction steps will ordinarily be used; while much less extraction solvent can be used in the second and third steps, the proportions of extraction solvent used in the subsequent extraction steps will usually be more than that designated above because the amount of DSDE remaining in the raffinate becomes increasingly small with each extraction, and a certain minimum amount of extraction solvent must be used in order to facilitate handling In the usual situation, about one-third to one-half of the amount of solvent used in the first extraction step will be used in the second, third, and (if needed) subsequent extraction steps. The Examples, below, illustrate the order of magnitude of the proportions of extraction solvent that have been used. The upper limit of the amount of extraction solvent used is dictated more by reasons of economic practicality than operability. However, it is rare that more than 5 ml of extraction solvent per gram of DSDE will be used for the first extraction step.

The amount of water used to facilitate the partitioning is dependent in part on the nature of the extraction solvent employed, increased solvent polarity requiring increased amounts of water. Since a preferred aim in carrying out the extraction is to produce a solution of sucrose-6-ester in a solvent such as DMF, which solution is suitable for direct chlorination by the method disclosed in U.S. patent application Ser. No. 382,147 wherein the solution should be anhydrous, it is important for economic reasons to minimize the amount of water employed. The table below shows data on the extraction of the tin compound distannoxane diacetate ("DSDA") from a 100 g sucrose input scale sucrose-6-acetate reaction mixture (produced by the method of Example 8, first 2 paragraphs), using variable amounts of cyclohexane and water. A single extraction step was used. In commercial practice, it is probable that more than one (e.g., two or three) extraction steps would be used.

| ML CYCLOHEXANE EXTRACTED | ML WATER | $H_2O$/DSDA MOL RATIO | GM DSDA REMAINING* | MOL % DSDA |
|---|---|---|---|---|
| 000 | 0 | — | 92.6 | 00.0 |
| 100 | 0 | — | 74.5 | 19.5 |
| 100 | 5 | 1.80 | 6.95 | 92.5 |
| 100 | 10 | 3.60 | 4.52 | 95 1 |
| 100 | 20 | 7.20 | 3.55 | 96.2 |
| 100 | 30 | 10.8 | 2.59 | 97.2 |
| 200 | 30 | 10.8 | 1.45 | 98.4 |

*Grams of DSDA remaining in the raffinate following extraction.

It can be seen that in the absence of water the extraction is inefficient, but that addition of only a small amount of water is sufficient to produce an efficient and effective partitioning of the tin species into the hydrocarbon phase. The total extraction feed (i.e., the DMF solution of S-6-A plus DSDA, not including the cyclohexane) comprised 540 g of solution which contained about 92.6 grams (0.154 mol) of DSDA. The preferred extraction solvents and water quantities employed in the practice of the invention are hydrocarbon solvents and from about three moles of water to about twenty moles of water per mole of DSDE present in the extraction mixture. The preferred extraction solvents are hexane, cyclohexane, and heptane, and the preferred proportions of water are from about five to about ten moles of water per mole of DSDE.

The fact that the efficient partitioning of the DSDE into the organic phase requires the addition of small amounts of water (molar basis DSDE) to the polar aprotic phase is surprising and could not have been predicted by those skilled in the art. The effectiveness of the water in producing favorable DSDE partitioning behavior may be due, in part, to the possible destruction of associative interactions between the DSDE and the various carbohydrate species present. [Tetravalent organotin compounds have a propensity for forming penta- and hexacoordinate species if groups with ligand properties, such as hydroxyls, are present. For leading references, see S. David and S. Hanessian, *Tetrahedron*, 41, 643 (1985) and A. Davies, et al., *J. Chem. Soc. Dalton Trans.*, 297 (1986).] At any rate, following water addition, the DSDE is extracted from the polar aprotic phase into the relatively nonpolar organic phase and isolated as a monohydrate, suggesting that the added water breaks down DSDE-carbohydrate associations producing readily extractable $DSDE.H_2O$ species.

The Examples below illustrate the practice of the invention.

EXAMPLE 1

Preparation of Sucrose-6-Benozoate by the Method of Navia with Extractive Removal of DSDB by Cyclohexane and Water To a 500-ml, 4-neck, round-bottom flask, equipped with mechanical stirring, thermometer, condenser, and a Dean-Stark trap, was charged 5.16 g (87.4% assay, 80.4 mmol) of potassium hydroxide, 100 ml of n-butyl alcohol, and 35 ml of hexane, and the mixture was heated to reflux. Water (about 2.5 ml) was collected in the Dean-Stark trap as a hexane azeotrope as it formed over a 45 min period. To the reactor contents was then added a solution of 32.2 g (44.5 mmol) of distannoxane dibenzoate ("DSDB", prepared as described below in Example 6A) in 50 ml of hot hexane. The mixture was maintained at reflux for 30 min while the hexane was distilled out. The hot reaction mixture was vacuum filtered directly into another 500-ml round-bottom flask, equipped as described above, care being taken to exclude atmospheric moisture. The filter cake was washed twice with a total of 100 ml of a 1:1 (by volume) mixture of butanol and hexane. The solid potassium benzoate (12.4 g dry weight, 96.6% of theory) was discarded.

To the cloudy filtrate [containing 1,3-dibutoxy-1,1,3,3-tetrabutyldistannoxane ("DBDS") in butanol] was added 25.0 g (73.1 mmol) of sucrose dissolved in 150 ml of hot (about 90° C.) DMF. The reactor was fitted for vacuum distillation and distillate was collected at 65°–66° C. head temperature (70°–73° C. vessel temperature) under water-aspirator vacuum. After removal of about 200 ml of distillate, an additional 50 ml of DMF was added to the vessel. Distillation was continued until a total of 312 ml of distillate was collected. The distillation residue was diluted with 50 ml of DMF to yield a clear pale-yellow solution of 1,3-di-(6-O-sucrose)-1,1,3,3-tetrabutyldistannoxane ("DBSS") in DMF (volume about 130 ml).

The solution was cooled to 18°–20° C. and treated in a single portion with 18.2 g (80.6 mmol) of benzoic anhydride. After stirring overnight, the reaction mixture was transferred to a separatory funnel and treated with 50 ml of cyclohexane and 5 ml (278 mmol, 6.24 equiv basis DSDB) of water. The contents of the separator were agitated gently and the resulting phases allowed to separate. The top phase was removed and the bottom (DMF) phase extracted with additional cyclohexane (5×50 ml). Concentration of the combined extracts afforded 35.0 g of recovered DSDB (containing residual solvent) as a viscous yellow oil which solidified on standing. The bottom phase was concentrated in vacuo at 50° C. to a thick yellow syrup (46.1 g) shown by HPLC analysis to contain 59.5% w/w sucrose-6-benzoate (27.4 g, 61.4 mmol, 84.1% yield), 6.4% w/w sucrose dibenzoates, and 0.7% w/w residual sucrose. Residual tin by atomic absorption spectrophotometry, expressed as percent DSDB, was 0.9% w/w.

EXAMPLE 2

Extractive DSDB Removal From a Crude Sucrose-6-Benzoate Mixture Employing Methyl t-Butyl Ether With Added Water In a sequence identical to that employed in Example 1, a crude reaction mixture containing DSDB and S-6-B was treated with 5 ml (278 mmol, 6.24 equiv basis DSDB) of water and then extracted with methyl t-butyl ether (MTBE, 6×100 ml). The combined extracts, which were found to contain some S-6-B by silica-gel TLC ($R_f$ about 0.5, 15:10:2, $CHCl_3$—$CH_3OH$—$H_2O$, sprayed with 5% ethanolic $H_2SO_4$ and charred), were backwashed with 50 ml of water, and the aqueous phase combined with the raffinate from the previous extractions. Concentration of the combined MTBE extracts afforded 33.4 g of recovered DSDB (containing residual solvent) as a thick syrup which solidified on standing. The combined bottom phases were concentrated in vacuo at 50° C. to yield 46.6 g of a pale-yellow syrup found by HPLC analysis to contain 58.2% w/w sucrose-6-benzoate (27.1 g, 60.8 mmol, 83.3% yield) and 0.3% w/w residual sucrose. The S-6-B accounted for 100% of sucrose monobenzoates and 87.4% of all benzoylated carbohydrate species. Residual tin in the sample was assayed by atomic absorption spectrophotometry and found to be 0.14% w/w expressed as percent DSDB.

EXAMPLE 3

Extractive DSDB Removal From a Crude Sucrose-6-Benzoate Mixture Employing Cumene With Added Water In a procedure performed in the same manner as the preceding examples, a crude reaction mixture of sucrose-6-benzoate and DSDB was prepared (volume about 170 ml), and treated with 100 ml of cumene (isopropyl benzene) and 10 ml (556 mmol, 12.5 equiv basis DSDB) of water. The cloudy biphasic system was mixed thoroughly and allowed to stand to produce two clear liquid phases. They were separated, and the raffinate extracted with additional cumene (3×100 ml). The raffinate was concentrated at 50° C. in vacuo to give 46.5 g of a syrup found by HPLC analysis to contain 50.6% w/w S-6-B (23.5 g, 52.7 mmol, 72.1% yield), 3.6% w/w residual sucrose, and 6.0% w/w sucrose dibenzoates. Sucrose-6-benzoate accounted for 100% of the monobenzoates and 91.2% of the total benzoylated carbohydrate fraction. The residual tin, expressed as % DSDB, was 0.04% (atomic absorption analysis).

EXAMPLE 4

Preparation of Sucrose-6-Benzoate With Extractive Removal of DSDB by Methyl t-Butyl Ether/Cyclohexane and Added Water In a sequence identical to that employed in Example 1, a crude reaction mixture containing DSDB and sucrose-6-benzoate was treated with 5 ml (278 mmol, 6.24 equiv basis DSDB) of water and then extracted with a 1:1 (by volume) mixture of MTBE and cyclohexane (6×50 ml). The combined extracts yielded, on evaporation, 35.0 g of DSDB (containing residual solvent). The raffinate was concentrated in vacuo at 50° C. to a syrup (46.1 g) shown by HPLC analysis to contain 59.5% w/w S-6-B (27.4 g, 61.4 mmol, 84.1% yield). Residual DSDB in the syrup was 0.4 g.

EXAMPLE 5

Recycle Experiments Utilizing Extractively Recovered DSDB

Table 1 summarizes the results of a series of experiments preparing sucrose-6-benzoate using extractively recovered DSDB. The method was analogous to that recorded in Example 1, on a two-fold larger scale. The initial DSDB charge was prepared by the method of Example 6A, using benzoic anhydride, and isolating by crystallization from 5% aqueous acetonitrile, and the remaining DSDB charges were prepared by using recycled DSDB from the previous cycle.

Tin reagent recoveries over 6 cycles averaged 97.7%, the deficit being caused by losses to the potassium benzoate filter cake and by mechanical losses. The sucrose-6benzoate yields averaged 87.7%, based upon initial sucrose charge.

This Example is an illustration of the aspect of the invention wherein the distannoxane diester extraction product is first reacted with alcoholic alkali to produce a 1,3-di(hydrocarbyloxy)-1,1,3,3-tetra(hydrocarbyl)distannoxane, which is then used in the process of Navia to produce a 1,3-di-(6-O-sucrose)-1,1,3,3-tetra(hydrocarbyl)distannoxane, which is then reacted with an acylating agent to generate a sucrose-6-ester and distannoxane diester. This process may then be repeated in commercial practice. In this experiment, the 1,3-di(hydrocarbyloxy)-1,1,3,3-tetra(hydrocarbyl)distannoxane produced is a 1,3-dialkoxy-1,1,3,3-tetra(alkyl)distannoxane, specifically, 1,3-dibutoxy-1,1,3,3-tetrabutyldistannoxane.

TABLE 1
RESULTS OF EXPERIMENTS PREPARING SUCROSE-6-BENZOATE VIA THEPROCESS OF EXAMPLE 1 WITH RECYCLE OF THE DISTANNOXANE DIBENZOATE TO THE SUBSEQUENT BATCH

| DSDB RECYCLE NO. | 1 | 2 | 3 | 4 | 5 | 6 | 7 |
|---|---|---|---|---|---|---|---|
| DSDB RECYCLED FROM CYCLE NO. | (a) 0 | 1 | 2 | 3 | 4 | 5 | 6 |
| RECYCLED DSDB (g) | — | 41.0 | 41.4 | 43.5 | 42.6 | 42.5 | 43.6 |
| FRESH DSDB (g) | 43.4 | 2.5 | 2.0 | 2.0 | 1.5 | 1.5 | 0.0 |
| DSDB RECOVERY (g) | 41.2 | 41.5 | 44.2 | 43.1 | 43.4 | 44.3 | 42.5 |
| DSDB RECOVERY (%) | 96.1 | 95.8 | 102.0 | 96.2 | 98.6 | 100.7 | 98.2 |
| SUCROSE-6-BENZOATE YIELD (%) | 92.8 | 90.5 | 86.9 | 83.6 | 84.5 | 85.8 | 83.2 |

(a)DSDB prepared by the method of Example 6A

EXAMPLE 6

Preparation of Distannnoxane Diesters (DSDE)

Two methods were employed to produce the distannoxane diesters used as standards and in the experiments reported in Examples 1-5.

A. From the carboxylic acid and dibutyltin oxide.

Dibutyltin oxide (DBTO, 100 g, 0.40 mol) was refluxed with acetic or benzoic acids (24.1 or 49.1 g, 0.40 mol) in toluene or cyclohexane (200 ml) and the water of reaction was separated in a Dean-Stark trap. Water removal took about 2 hours. The DSDE could be used in solution, or crystallized and isolated by solvent removal and dissolution in either 200 ml of 5% aqueous acetonitrile (DSDB) or 100 ml of 5% aqueous DMF (DSDA). The two distannoxane esters crystallized as monohydrates with the following characteristics:

|  | DSDA | DSDB |
|---|---|---|
| Yield (g) | 107 g | 126 g |
| M.P. (°C.) | 57-58[a] | — |
| Analysis: found C | 38.87 | 47.26 |
| H | 6.83 | 6.24 |
| Calc for $C_{20}H_{42}O_5Sn_2 \cdot H_2O$ | 39.39 6.83 | — |
| Calc for $C_{30}H_{46}O_5Sn_2 \cdot H_2O$ | — | 48.56 6.20 |

[a]Literature (D. L. Alletson et al., J. Chem. Soc., 5469, (1963), 58-60° C.

B. From the anhydride and dibutyltin oxide.

DBTO (100 g, 0.40 mol) was slurried in cyclohexane (200 ml) at 60° C. and acetic or benzoic anhydrides (20.4 or 45.2 g, 0.20 mol) was added. Stirring was continued for 2 hr at 60° C. by which time the DBTO had completely dissolved. The DSDE was either used in solution or isolated by the methods outlined in Method A to give products in the same yield and exhibiting the same properties as given above.

EXAMPLE 7

Preparation of Sucrose-6-Acetate From Dibutyltin Oxide Using the Process of Navia DBTO (114 g, 460 mmol) was refluxed for 2 hr in n-butanol (220 ml) and cyclohexane (50 ml) while 4.0 ml of water were collected in a Dean-Stark trap. A total of 230 ml of mixed solvents were then removed by vacuum distillation to afford a pale-brown slightly turbid oil which consisted of DBDS dissolved in n-butanol.

Sucrose (150 g, 438 mmol) was dissolved in DMF (450 ml) at 110° C., and the solution cooled to 90° C. and added to the above oil. Vacuum was reapplied and distillation was continued collecting 200 ml of distillate at a reaction vessel temperature of 80°-85° C. The distillation took about 30 min. DMF (100 ml, 80° C.) was added and vacuum distillation was continued collecting a further 150 ml distillate. This was repeated with 150 ml of DMF collecting an additional 100 ml distillate. The residue, which consisted of DBSS in DMF, was cooled to below 20° C.

Acetic anhydride (49.2 g, 482 mmol) was added dropwise at a rate sufficient to keep the temperature at 10°-20° C. using external cooling to control the exotherm. The addition took 40 min. The solution was stirred at 20°-25° C. for an additional 0.5 hr, then extracted with cyclohexane (3 × 250 ml), adding water (15 ml, 833 mmol, 3.62 equiv basis DSDA) to each of the first 2 extractions. The combined extracts (containing the DSDA) were stored for recycle, while the raffinate was concentrated in vacuo to 30% of the original weight to remove water, then diluted with DMF (100 ml) and stored for chlorination to sucralose-6-acetate. The solution (288 g) contained 98.2 g (256 mmol, 58.4% yield) of sucrose-6-acetate by HPLC assay. Atomic absorption spectrophotometry determined the solution contained 0.07% tin, equivalent to 0.4 g DBTO.

EXAMPLE 8

Extractive Organotin Recovery with Conversion to Dibutyltin Oxide for Recycle Using the Process of Neiditch Et. Al.

To a 1000-ml, 4-neck, round-bottom flask, equipped with mechanical stirrer, thermometer, 60-ml addition funnel, and distillation overheads consisting of a short Vigreux column, Dean-Stark distillation receiver, and reflux condenser, was charged 76.4 g (0.307 mol) of DBTO, 100 g (0.292 mol) of sucrose, and 350 ml of DMF. The mixture was heated to 100°-110° C. to dissolve the sucrose, then cooled to 85°-90° C. and cyclohexane (100 ml) added via the dropping funnel (gentle reflux). The mixture was heated at vigorous reflux (reaction temperature 90°-95° C.) for 4.5 hr while the lower aqueous phase in the Dean-Stark receiver was collected. Additional cyclohexane was added as necessary to maintain the temperature below 95° C.

The resulting clear-brown moisture-sensitive solution, which contained DBSS in a mixture of DMF and cyclohexane, was cooled to 0° C. and treated dropwise with 32.8 g (0.321 mol) of acetic anhydride while maintaining the temperature below 10° C. with ice-bath cooling. The mixture was then allowed to warm to 20°-25° C. and stir for 1 hour.

Water (25 ml, 1.39 mol, 9.05 equiv basis DSDA) and additional cyclohexane (250 ml, total cyclohexane content about 350 ml) were added and the mixture vigorously agitated for 10 min at 20°-25° C., and then transferred to a 1000-ml separatory funnel. The phases were separated, and the lower phase treated with additional water (25 ml, 1.39 mol, 9.05 equiv basis DSDA) and further extracted with cyclohexane (2×150 ml). The extraction process removed 99.5% of the total tin content. The DMF-based raffinate (containing S-6-A, water, and entrained cyclohexane) was then fractionally distilled at 50 mm of Hg and 70° C. (maximum) to remove the water and cyclohexane prior to HPLC analysis (96.1 g, 0.250 mol, 85.7% yield of S-6-A).

The cyclohexane extracts (containing DSDA) were combined and concentrated to an oil which was added hot (over 70° C.) in a thin stream over 5 min to a very vigorously agitated solution of 1.1 N aqueous sodium hydroxide (300 ml) at 95° C. Granules of DBTO were rapidly formed. The DBTO slurry was agitated vigorously at 90°-95° C. for 10-15 minutes, then cooled to 30° C. and filtered. The DBTO cake was thoroughly washed with water (3×100 ml) and dried (25-33% loss on drying).

The recovered DBTO was used to produce S-6-A by the procedure described above in this Example 8, with the DSDA being extracted, recovered as DBTO, and then again recycled to produce S-6-A by the process of Neiditch et al. Dibutyltin oxide recoveries (corrected for purity), yields of sucrose-6-acetate, and DBTO input composition data for the replicate experiments are presented below in Table 2. (Note that the DBTO was isolated as a hemihydrate.)

The preceding example is an illustration of that aspect of the invention wherein the recovered DSDE is treated with aqueous alkali and recovered as a di(hydrocarbyl)tin oxide (in this case, a dialkyltin oxide, and more specifically, dibutyltin oxide), which was then recycled to produce a sucrose-6-ester by the process of Neiditch et al. Said recovered tin oxide could also be employed for reuse in the process of Navia or the process of Walkup et al.

TABLE 2

PREPARATION OF SUCROSE-6-ACETATE BY THE PROCEDURE OF EXAMPLE 8 RECYCLING THE DISTANNOXANE DIACETATE TO THE SUBSEQUENT BATCH

| DSDB RECYCLE NO. | 1 | 2 | 3 | 4 | 5 | 6 |
|---|---|---|---|---|---|---|
| DSDB RECOVERED FROM CYCLE NO. | — | 1 | 2 | 3 | 4 | 5 |
| RECOVERED DBTO (g) | — | 72.0 | 80.0 | 80.0 | 80.1 | 78.2 |
| FRESH DBTO (g) | 77.1 | 6.9 | 3.1 | 0.0 | 0.0 | 2.5 |
| DBTO INPUT (EQUIV BASED ON SUCROSE, CORRECTED FOR ASSAYS) | 1.02 | 1.04 | 1.01 | 1.02 | 1.06 | 1.05 |
| SUCROSE-6-ACETATE YIELD (%) | 85.7 | 87.8 | 86.3 | 87.9 | 86.4 | 86.6 |
| DBTO RECOVERY (%) | 94.2 | 96.6 | 103.6 | 102.8 | 97.4 | 102.7 |

EXAMPLE 9

Chlorination of Crude Sucrose-6-Benzoate/DMF Mixture After Extractive Tin Reagent Recovery This Example illustrates the direct chlorination of the raffinate produced after DSDB extraction (in accordance with the practice of this invention) as an intermediate step in a process for preparing the high-intensity nonnutritive sweetener sucralose.

To a 500-ml, 4-neck, round-bottom flask, equipped with mechanical stirring, thermometer, condenser, argon blanket, and addition funnel, was charged 16.8 g of sucrose-6-benzoate (10.0 g, 22.4 mmol) syrup, prepared as described in Example 1 dissolved in 90 ml of dry DMF. To the resulting clear pale-yellow solution, cooled to −38° C., was added dropwise a total of 35.3 ml of phosgene (491 mmol) dissolved in 24 ml of toluene. The addition was exothermic with the internal temperature rising from −38° C. to +14° C. over the course of the addition.

The resulting slurry was warmed to 65° C., and the clear solution thus produced heated at 82°-83° C. for 1 and then at 112°-113° C. for 3 hours. The reaction mixture was cooled to 8° C. and treated with enough precooled (<5° C.) 4.0 N NaOH to raise the pH to 9-10 (116 ml). This addition was very exothermic with the temperature rising from 8° C. to 51° C. The mixture was stirred at pH 9-10 for 3 min, and then neutralized by the dropwise addition of acetic acid.

The mixture was extracted with ethyl acetate (4×200 ml), and the combined extracts washed with 150 ml of water and decolorized at 45° C. with 4 g of charcoal. The yellow filtrate was concentrated in vacuo at 50° C. to a residual orange syrup which was treated with 50 ml of water and 50 ml of MTBE, and warmed to 50° C. The biphasic mixture was seeded, agitated thoroughly, and cooled to ambient temperature whereupon sucralose-6-benzoate crystallized. The solid was collected by suction filtration, washed twice with a total of 50 ml of MTBE, and dried in vacuo at 50° C. to yield 6.17 g of an off-white solid. HPLC analysis showed the product to contain 91.5% w/w sucralose-6-benzoate (5.65 g, 11.3 mmol, 50.2% yield). The mother liquors from the crystallization were concentrated to afford 7.28 g of a syrup found to contain 28.8% w/w product by HPLC assay (18.6% yield).

EXAMPLE 10

Chlorination of Crude Sucrose-6-Acetate/DMF Syrup After Extractive Tin Removal

This example is a further illustration of the direct chlorination of the raffinate following DSDA extraction (in accordance with the practice of this invention) as an intermediate step in sucralose production.

To a 1000-ml, 4-neck, round-bottom flask, equipped with overhead stirrer, thermometer, argon inlet, and vacuum distillation equipment, was charge 105 g of sucrose-6-acetate syrup (39.5 g, 103 mmol, prepared and freed from DSDA as described in Example 8) and 272 g of DMF. The resulting solution was vacuum distilled (3–5 Torr) at 35° C. to remove adventitious moisture and residual volatiles. A total of about 70.5 g of distillate was collected.

The residue (298 g) was cooled to about 0° C. and treated portionwise with stirring with 121 g (943 mmol) of commercial (Aldrich Chem. Co.) chloromethylene(-dimethylammonium) chloride between 0° C. and 32° C. (exothermic). The mixture was heated to 114° C. over about 30 min and maintained at that temperature for 3 hr. The reaction was cooled to 0° C., and treated in a single portion with 238 g of cold (0°–5° C.) aqueous 16 wt % sodium hydroxide (final pH 9–10). The heat of reaction raised the temperature to 54° C. The mixture was neutralized (to pH 7) with concentrated hydrochloric acid, treated with 14 g of decolorizing carbon, and filtered through a bed of filter aid.

The DMF was removed from the product mixture by steam distillation. The aqueous solution, containing sucralose-6-acetate, was concentrated at 50° C. under reduced pressure, treated with 10 g of decolorizing carbon, and filtered through filter aid. The filtrate was extracted with ethyl acetate (2×500 ml followed by 1×300 ml). The combined ethyl acetate extracts were washed with 150 ml of water and concentrated to a syrup (61.1 g) which began to crystallize spontaneously.

The semisolid residue was triturated with MTBE (100 ml). The resulting solid was collected by vacuum filtration and dried in vacuo at ambient temperature to yield 26.8 g of sucralose-6-acetate (70.6% w/w, 18.9 g, 43.0 mmol, 41.7% yield) containing 15% w/w occluded solvent. An additional 2.2% yield of product was contained in the mother liquors.

EXAMPLE 11

Conversion of Recrystallized Sucralose-6-Benzoate to Sucralose

To a 2000-ml, 4-neck, round-bottom flask, equipped with overhead stirrer, thermometer, drying tube, and stopper, was charged 207 g of 91.4% sucralose-6-benzoate (189 g, 378 mmol, produced as described above in Example 9) and 1000 ml of methanol. The mixture was heated to dissolve the solids, 25 ml of 0.84 M potassium hydroxide (21 mmol) in methanol added in a single portion, and stirring conducted at room temperature for 5 hours.

The reaction mixture was neutralized by the addition of a weak-acid ion-exchange resin (acid form). The solution was filtered and the resin washed with methanol (2×250 ml). The combined filtrates were evaporated to a soft foam (245 g) which was dissolved in 1000 ml of water and extracted with ethyl acetate (3×250 ml) to remove methyl benzoate, unreacted sucralose-6-benzoate, and other nonpolar impurities. The aqueous layer was concentrated to a viscous light-brown solution (487 g, 29.0 wt % sucralose, 94.0% crude yield) which was decolorized with charcoal. The solution was concentrated in vacuo to 181 g at 70° C., and crystallization completed by allowing the solution to first cool gradually to 40° C. over 3.5–4.0 hr, followed by cooling at 10° C. for 1.5 hr. Product was recovered by vacuum filtration and dried at 45°–50° C. in vacuo to give 112 g (282 mmol, 74.5% yield) of sucralose [mp 119°–120° C., decomp; [α]20°/D +87.1° (C, 1.23, H$_2$O)]. The colorless crystalline product had an HPLC purity of 99.6 wt %.

EXAMPLE 12

Deacetylation of Sucralose-6-Acetate

Crude crystalline sucralose-6-acetate (114 g, 258 mmol, produced as described above in Example 10) was dissolved in 400 ml of methanol in a 1000-ml, 4-neck flask fitted with overhead stirring, thermometer, reflux condenser, and stopper. The solution was warmed to 55°–60° C. with an oil bath and 3.5 ml of 30 w/v % KOH in methanol were added. TLC (80:17:3, CHCl$_3$—CH$_3$OH—HOAc, sprayed with 5% ethanolic H$_2$SO$_4$ and charred) after 15 min indicated the reaction was essentially complete. After a further 15 min reaction time, the mixture was neutralized with 40 g of methanol-washed weak-acid ion-exchange resin (acid form).

The resin was removed by filtration and washed with two 100-ml portions of methanol. The combined filtrate and washes were evaporated to a thick syrup which was diluted with water and further concentrated to remove residual methanol. The residue was decolorized with carbon and concentrated in vacuo at 60° C. Crystallization of the product was carried out by allowing the stirred seeded syrup to gradually cool to ambient temperature overnight. Recovery amounted to 80.5 g (dry weight) of 96.6% pure sucralose (77.8 g, 195 mmol, 75.6% yield). A further 21.0 g (52.8 mmol, 15.9% yield) of sucralose were retained in the mother liquor.

Outlines of the processes of Navia, Neiditch et al., and Walkup et al. are set forth below.

The process of Navia comprises the reaction of a 1,3-di(hydrocarbyloxy)-1,1,3,3-tetra(hydrocarbyl)distannoxane [which will be referred to for brevity as a "di(hydrocarbyloxy)-distannoxane"] with sucrose to form a 1,3-di-(6-O-sucrose)-1,1,3,3-tetra(hydrocarbyl)-distannoxane [which will be referred to for brevity as a "di(hydrocarbyl)stannoxylsucrose"], which is then reacted with an acylating agent to form a sucrose-6-ester. A byproduct of this reaction is a 1,3-diacyloxy-1,1,3,3-tetra(hydrocarbyl)distannoxane or distannoxane diester. The two reactions are illustrated with the following generalized experimental procedure in which DBTO is used to generate the di(hydrocarbyloxy)distannoxane in situ, and benzoic anhydride is used as the acylating agent:

Methanol (100 ml), sucrose (5.00 g), and dibutyltin oxide (3.64 g, 1.00 mol equiv basis sucrose) are charged to a suitable reaction vessel. The contents of the reaction vessel are refluxed for about 2 hr and the methanol evaporated. The product of this reaction is 1,3-di-(6-O-sucrose)-1,1,3,3-tetrabutyldistannoxane. The white solid is taken up in DMF (100 ml) and 3.64 g of benzoic anhydride (about 1.10 mol equiv basis sucrose) is added. The contents of the reaction vessel are stirred at room temperature overnight. The product is a sucrose-6-ester (in this case S-6-B), with a DSDE (in this case DSDB) being produced as a byproduct.

The sucrose and di(hydrocarbyloxy)distannoxane reactants are employed in proportions so as to produce the desired 1,3-di-(6-O-sucrose)-1,1,3,3-tetra(hydrocarbyl)distannoxane. In the preferred mode of carrying out the process of Navia wherein the di(hydrocarbyloxy)-distannoxane is generated in situ by the reaction of a di(hydrocarbyl)tin oxide ("DHTO") with a lower alkanol such as methanol, the DHTO and sucrose are preferably employed in stoichiometric ratios of about one-to-one. This is because the use of an excess of sucrose leads to contamination of the S-6-E by sucrose and undesired sucrose esters, while the use of excess DHTO causes contamination of the S-6-E product by sucrose diesters. The most preferred stoichiometric ratio uses the DHTO in a very slight (1-3%) molar excess (basis sucrose) in order to insure the near absence of sucrose in the product.

In place of the DBTO there can be used other di(hydrocarbyl)tin oxides in which the hydrocarbyl groups bonded to tin can be, individually, alkyl, cycloalkyl, aryl, or arylalkyl such as, for example, methyl, ethyl, propyl, butyl, octyl, benzyl, phenethyl, phenyl, naphthyl, cyclohexyl, and substituted phenyl. The preferred hydrocarbyl groups are alkyl having up to eight carbon atoms. In place of the tin oxide, a di(hydrocarbyl)tin dialkoxide, dihalide, diacylate, or other organic tin compound can be used as long as it generates the di(hydrocarbyloxy)distannoxane in situ.

The reaction is carried out in an organic liquid reaction medium that is a solvent for suorose and the di(hydrocarbyloxy)-distannoxane. When the di(hydrocarbyloxy)distannoxane is generated in situ, the reaction medium is preferably also a solvent for the compound(s) that are used to generate the di(hydrocarbyloxy)distannoxane. More preferably, the reaction medium is also one of the reactants that are used to generate the di(hydrocarbyloxy)distannoxane in situ. A wide variety of aliphatic and cycloaliphatic alcohols or phenols can be used as the reaction medium. It is often most economical to carry out the reaction between the DHTO (or equivalent reactant) and the alcohol or phenol under atmospheric reflux conditions. For this purpose, lower alkyl primary alcohols are generally preferred. Thus, the preferred reaction mediums are primary lower alkanols such as methanol, ethanol, n-propanol, n-butanol, n-pentanol, and n-hexanol. Additional alcohols and phenols that may be used as the reactant/reaction medium include phenol, substituted phenols such as lower alkyl-substituted phenols, cyclohexanol and substituted cyclohexanols such as lower alkyl-substituted cyclohexanols. Inert organic liquids such as toluene, xylene, and other hydrocarbons may be used as diluents in the reaction, if desired.

The reaction between sucrose and the di(hydrocarbyloxy)distannoxane is carried out at a temperature and for a period of time sufficient to form a di(hydrocarbyl)-stannoxylsucrose. Illustrative reaction temperatures are within the range of from about 50° C. to about 100° C. Illustrative reaction times are from about 1 to about 24 hours. The di(hydrocarbyl)stannoxylsucrose is recovered by evaporating the reaction medium, which may be performed under reduced pressure if desired. The di(hydrocarbyl)stannoxylsucrose product of the evaporation is used directly without further purification in the acylation reaction.

It is preferred to employ slightly (1-5%) more than one molar equivalent of acylating agent (basis sucrose). The selection of the particular acylating agent to be used in the acylation reaction is dictated in part by the use to which the acylated product is to be put. For example, if the acyl group is being employed as a blocking group, as it would be in the preparation of the artificial sweetener as discussed above in the Background of the Invention section of this application, an acylating agent such as benzoic or acetic anhydride would be employed because it is inexpensive, the acyl group is readily removed at an appropriate stage of the synthesis, and it is stable to reactions that the acylated compound must undergo prior to removal of the acyl group. If a S-6-E is to be the ultimate product of the synthesis, then the acylating agent used is the one that will generate the desired acyl group for the ester product.

With these principles in mind, among the acylating agents that can be used are the various anhydrides of benzoic and substituted benzoic acid (e.g., 4-nitrobenzoic acid, 3,5-dinitro-benzoic acid, and the like), alkanoic acids such as acetic acid, propionic acid, butyric acid, cyclohexanecarboxylic acid, long chain fatty acids, both saturated and unsaturated, such as stearic acid, oleic acid, linoleic acid, and the like, having up to, for example, 28 carbon atoms, unsaturated acids such as acrylic acid and methacrylic acid, substituted acids such chloroacetic acid, cyanoacetic acid, phenoxyacetic acid, and the like, and saturated and unsaturated dicarboxylic acids such as phthalic acid, maleic acid, glutaric acid, and the like.

The acylation reaction is carried out in an inert organic reaction vehicle such as DMF or other polar aprotic solvents such as DMSO, NMP, DMF, HMPA, and other polar aprotic solvents in which sucrose is soluble. DMF is the preferred polar aprotic solvent because of its low cost, its relatively low boiling point, and its suitability as a solvent for further steps in the process for producing sucralose. The acylation reaction is carried out at a temperature and for a period of time sufficient to prepare the S-6-E product.

If the anhydride is a liquid, it may be added neat to the sucrose-organotin adduct, or it may be diluted with an inert cosolvent. If the anhydride is a solid, it may be added in the solid form or added as a solution in an appropriate inert solvent. The anhydride may be added all at once, or it may be added slowly over a period of time.

Anhydride stoichiometry is an important aspect of the successful practice of this invention. The use of too little anhydride will result in a S-6-E product contaminated by residual sucrose. The use of too much anhydride will cause sucrose diester contamination. The most preferred stoichiometric ratio uses the anhydride in a slight (5-10%) molar excess (basis sucrose) in order to insure the near absence of sucrose in the product.

Acylation temperatures from below 0° C. to about 30° C. have been employed experimentally. The upper limit of acceptable acylation temperatures is governed by the onset of thermally activated nonregioselective acylation reactions which will result in the formation of undesirable sucrose mono- and diesters. From a practical standpoint, this temperature limit is a function of the reactivity of the acid anhydride. For example, because acetic anhydride is a relatively reactive species, acylations with it are normally carried out below about 20° C. Benzoic anhydride, on the other hand, being somewhat less reactive, allows for acylation at room temperature or slightly above.

The acylation reactions are mildly exothermic. Depending upon initial reaction temperature and rate of anhydride addition to the di(hydrocarbyl)tin-sucrose adduct, external cooling of the acylation process might be required in order that thermally activated nonregioselective acylation be minimized.

The times required for the acylations of the sucrose adducts to go to completion are dependent upon the concentration of the reactants (as the acylation is a multiple-order process), the reactivity of the acylating agent, and the temperature of the reaction mixture. Although times of from one hour to several days have been employed in the laboratory, there is no advantage to extending the reaction period longer than that time necessary for consumption of the acylating agent. This is generally complete within from about one to about five hours under typical conditions.

The process of Neiditch et al. is outlined as follows:

The process is carried out by reacting sucrose with a di(hydrocarbyl)tin oxide in an inert organic vehicle. The DHTO's that can be used are those described above with respect to the process of Navia.

The DHTO and sucrose may be employed in a wide range of stoichiometric ratios. However, stoichiometric ratios of about one-to-one are preferred. This is because the use of an excess of sucrose leads to contamination of the S-6-E by sucrose and undesired sucrose esters, while the use of excess DHTO causes contamination of the S-6-E product by sucrose diesters. The most preferred stoichiometric ratio uses the DHTO in a very slight (1–3%) molar excess (basis sucrose) in order to insure the near absence of sucrose in the product.

The process of Neiditch et al. is carried out in an inert organic reaction vehicle. By "inert" is meant that the reaction vehicle is free of any organic functional groups that will react with either the sucrose or the DHTO. In many cases, in order to accomplish the objectives of the invention, the inert organic reaction vehicle will be a mixed solvent system comprising a polar aprotic solvent and a cosolvent. The polar aprotic solvent is employed for the purpose of dissolving the sucrose, and the cosolvent is employed for the purpose of codistillatively removing all water generated by the reaction of sucrose with the DHTO and also promoting the solubility of the DHTO. The polar aprotic solvents which can be employed include are those that were described above with respect to the process of Navia. DMF is the preferred polar aprotic solvent.

Cosolvents capable of codistillatively removing the water of condensation include chlorinated hydrocarbons such as chloroform, a variety of saturated and aromatic hydrocarbons such as hexane, heptane, octane, cyclohexane, benzene, and toluene, ketones such as methyl ethyl ketone and methyl isobutyl ketone, acyclic and cyclic ethers such as tetrahydrofuran, and other inert organic liquids that meet the criteria set forth herein. A very wide range of organic liquids are suitable for use as cosolvents in the invention. The primary criteria for a cosolvent are (1) that is produce a mixture with the polar aprotic solvent, the DHTO, and the sucrose, which refluxes at atmospheric pressure with an internal reaction temperature within the range of from about 75° C. to about 125° C., (2) that it codistill the water produced by the condensation of the DHTO and sucrose, thereby facilitating removal of water during the reaction, and (3) that it promote the solubility of the DHTO in the reaction mixture (since DHTO's are usually not soluble to any significant degree in polar aprotic solvents) and thereby enhance the rate of reaction of the DHTO with sucrose.

Cosolvents which are immiscible with water and which do form a constant-composition minimum-boiling azeotrope with water are preferred, but, as has been determined by experimentation, reaction systems employing such cosolvents typically reflux at temperatures significantly higher than either the water-azeotrope boiling point or the boiling point of the pure solvent. There is also data showing that the water-cosolvent compositions of the distillates arising from these systems are not constant throughout the DHTO-sucrose condensation period.

Preferred cosolvents for reasons of chemical stability, efficiency of water removal, cost, and boiling point include cyclohexane, n-heptane, and isooctane (2,2,4-trimethylpentane).

The reaction between sucrose and the DHTO is carried out at a temperature within the range of from about 75° C. to about 125° C. Below 75° C., the reaction becomes uneconomically slow, and above 125° C. there is a tendency for the carbohydrate to decompose. The preferred reaction temperature is within the range of about 80° C. to about 100° C., and more preferably, from about 85° C. to about 90° C.

The product of the reaction of sucrose and DHTO is a di(hydrocarbyl)stannoxylsucrose, the same product as in the Navia process. This product is acylated as in the Navia process, with the same product mixture being produced (i.e., a sucrose-6-ester and a DSDE byproduct).

The process of Walkup et al. is outlined as follows:

The first step in the process comprises the reaction of a DHTO with a dihydric alcohol, an alkanolamine, or an enolizable α-hydroxy ketone in an inert organic vehicle such as a normally liquid hydrocarbon, with removal of water, at a temperature and for a period of time sufficient to produce a cyclic adduct of said dihydric alcohol, alkanolamine, or α-hydroxy ketone. The inert organic vehicle employed is preferably one that is capable of removing water by azeotropic distillation. Hydrocarbons having boiling points between about 80° C. and 145° C. are preferred. Specific illustrative examples of such inert organic vehicles are cyclohexane, benzene, toluene, any of the xylenes, or mixtures thereof.

The di(hydrocarbyl)tin oxides employed in the Walkup et al. process are the same as those disclosed above with respect to the Navia process. The DHTO is reacted with a dihydric alcohol, an alkanolamine, or an α-hydroxy ketone. Specific illustrative examples of dihydric alcohols include alkane diols such as ethylene glycol, 2,3-propanediol, 2,3-butanediol, 1,3-butanediol, 1,4-butanediol, 1,3-propanediol, 1,2-pentanediol, 1,2-hexanediol, and other alkane diols that contain, for example, up to about eight carbon atoms, and cycloalkane diols such as 1,2-cyclohexanediol, 1,2-cyclopentanediol, and the like. Preferably, the hydroxyl groups on the dihydric alcohol are not more than four carbon atoms distant from each other on the carbon chain to which they are bonded. Specific illustrative examples of alkanolamines that can be used include ethanolamine, 2-amino-1-propanol, and 1-amino-2-propanol. Preferably, the amino and hydroxyl groups on the alkanolamine are not more than four carbon atoms distant from each other on the carbon chain to which they are bonded. Specific illustrative examples of α-hydroxy ketones that are capable of enolization to enediols include benzoin (2-hydroxy-2-phenylacetophenone) and acetoin (3-hydroxy-2-butanone). The preferred compounds for use in reacting with the DHTO are the alkane diols, particularly, ethylene glycol, since it gives excellent yields and is itself inexpensive.

The DHTO, which is normally insoluble in the inert organic reaction vehicle employed, may be suspended in the vehicle. The diol, alkanolamine, or α-hydroxy ketone (in slight stoichiometric excess) to be employed for the adduct formation is then added and the mixture is heated to reflux, which is normally at a temperature of from about 80° C. to about 145° C. Water is removed azeotropically as it formed as a result of the condensation between the di(hydrocarbyl)tin oxide and the diol, alkanolamine, or α-hydroxy ketone to afford homogeneous colorless solutions of the cyclic adducts. Reaction times of from about two to about four hours are typical for this step.

These intermediates may then be isolated by concentration and crystallization. It is usually more convenient to evaporate the solvent to produce a solid or a semi-solid di(hydrocarbyl)tin adduct, which is then dispersed in DMF or another solvent in which sucrose has an appropriate degree of solubility, which is used as the reaction medium for Step (b) of the process of the invention. Such solvents include DMF, DMSO, DMA, and the like, and other polar aprotic solvents in which sucrose is soluble, as discussed above.

In Step (b), sucrose is added to the reaction mixture which comprises the adduct product of Step (a) and the inert organic reaction vehicle such as DMF. The resulting suspension is stirred at ambient temperature for a period of time sufficient to form the 6-O-[dihydrocarbyl(hydroxy- or amino- or oxohydrocarbyl)stannoxyl]-sucrose intermediate, which usually takes from about twelve to about twenty-four hours. Alternatively, heating (e.g., up to about 85° C.) may be applied to increase the sucrose dissolution rate and shorten reaction time to about sixty minutes.

In Step (c), the usually turbid mixtures, which contain the reactive 6-O-[dihydrocarbyl(hydroxy- or amino- or oxohydrocarbyl)stannoxyl]sucrose intermediate and which comprise the product of Step (b), are then treated with two molar equivalents of an acylating agent such as a carboxylic acid anhydride at ambient temperature. The mixtures are stirred and monitored by TLC until acylation is judged to be complete (typically from about two to about seven hours). These turbid mixtures usually become crystal clear during this phase of the process.

The mixtures are quenched by the addition of water or methanol, filtered if necessary to remove any extraneous solids, extracted if desired to remove di(hydrocarbyl)tin byproducts, concentrated to a residual gum or oil with mild heating under reduced pressure, and then further processed and assayed as necessary (function of acyl group) prior to further processing, such as chlorination when the S-6-E is to be used in the production of sucralose.

What is claimed is:

1. A process which comprises extracting 1,3-diacyloxy-1,1,3,3-tetra(hydrocarbyl)distannoxane from a mixture containing 1,3-diacyloxy-1,1,3,3-tetra(hydrocarbyl)distannoxane, a sucrose-6-ester, and polar aprotic solvent, which process comprises the steps of:
   (a) contacting said mixture, in the presence of a small amount of water, with an organic solvent that is substantially immiscible with water to form thereby an extraction mixture, wherein the amount of water employed is sufficient to cause efficient partitioning of said 1,3-diacyloxy-1,1,3,3-tetra(hydrocarbyl)distannoxane from a first phase comprising said polar aprotic solvent into second phase comprising said organic solvent;
   (b) agitating the extraction mixture for a period of time and at a temperature sufficient to form thereby a two-phase mixture wherein the preponderance of the 1,3-diacyloxy-1,1,3,3-tetra(hydrocarbyl)distannoxane in the extraction mixture is contained in said second phase and essentially all of the sucrose-6-ester in the extraction mixture is contained in said first phase; and
   (c) separating said first phase from said second phase.

2. Process of claim 1 wherein the polar aprotic solvent is N,N-dimethylformamide.

3. Process of claim 1 wherein said organic solvent is a member of the group consisting of hydrocarbons, ethers, chlorinated hydrocarbons, ketones, and esters.

4. Process of claim 2 wherein said organic solvent is a member of the group consisting of hydrocarbons, ethers, chlorinated hydrocarbons, ketones, and esters.

5. Process of claim 1 wherein said organic solvent is an aliphatic hydrocarbon.

6. Process of claim 2 wherein said organic solvent is an aliphatic hydrocarbon.

7. Process of claim 5 wherein the aliphatic hydrocarbon is hexane, cyclohexane, or heptane.

8. Process of claim 6 wherein the aliphatic hydrocarbon is hexane, cyclohexane, or heptane.

9. Process of claim 1 wherein said organic solvent is cumene or methyl t-butyl ether.

10. Process of claim 2 wherein said organic solvent is cumene or methyl t-butyl ether.

11. Process of claim 1 wherein the 1,3-diacyloxy-1,1,3,3-tetra(hydrocarbyl)distannoxane is a 1,3-diacyloxy-1,1,3,3-tetra(alkyl)distannoxane.

12. Process of claim 2 wherein the 1,3-diacyloxy-1,1,3,3-tetra(hydrocarbyl)distannoxane is a 1,3-diacyloxy-1,1,3,3-tetra(alkyl)distannoxane.

13. Process of claim 5 wherein the 1,3-diacyloxy-1,1,3,3-tetra(hydrocarbyl)distannoxane is a 1,3-diacyloxy-1,1,3,3-tetra(alkyl)distannoxane.

14. Process of claim 6 wherein the 1,3-diacyloxy-1,1,3,3-tetra(hydrocarbyl)distannoxane is a 1,3-diacyloxy-1,1,3,3-tetra(alkyl)distannoxane.

15. Process of claim 7 wherein the 1,3-diacyloxy-1,1,3,3-tetra(hydrocarbyl)distannoxane is a 1,3-diacyloxy-1,1,3,3-tetra(alkyl)distannoxane.

16. Process of claim 8 wherein the 1,3-diacyloxy-1,1,3,3-tetra(hydrocarbyl)distannoxane is a 1,3-diacyloxy-1,1,3,3-tetra(alkyl)distannoxane.

17. Process of claim 11 wherein the 1,3-diacyloxy-1,1,3,3-tetra(alkyl)distannoxane is a 1,3-diacyloxy-1,1,3,3-tetrabutyldistannoxane.

18. Process of claim 12 wherein the 1,3-diacyloxy-1,1,3,3-tetra(alkyl)distannoxane is a 1,3-diacyloxy-1,1,3,3-tetrabutyldistannoxane.

19. Process of claim 1 wherein the acyloxy groups in the 1,3-diacyloxy-1,1,3,3-tetra(hydrocarbyl)distannoxane are acetoxy or benzoyloxy groups.

20. Process of claim 2 wherein the acyloxy groups in the 1,3-diacyloxy-1,1,3,3-tetra(hydrocarbyl)distannoxane are acetoxy or benzoyloxy groups.

21. Process of claim 15 wherein the acyloxy groups in the 1,3-diacyloxy-1,1,3,3-tetra(hydrocarbyl)distannoxane are acetoxy or benzoyloxy groups.

22. Process of claim 16 wherein the acyl groups in the 1,3-diacyloxy-1,1,3,3-tetra(hydrocarbyl)distannoxane are acetoxy or benzoyloxy groups.

23. Process of claim 1 wherein the 1,3-diacyloxy-1,1,3,3-tetra(hydrocarbyl)distannoxane product is subjected to the additional step of reaction with alcoholic alkali to produce thereby a 1,3-dialkyloxy-1,1,3,3-tetra(hydrocarbyl)distannoxane 24. Process of claim 11 wherein the 1,3-diacyloxy-1,1,3,3-tetra(alkyl)distannoxane product is subjected to the additional step of reaction with alcoholic alkali to produce thereby a 1,3-dialkyloxy-1,1,3,3-tetra(alkyl)distannoxane.

25. Process of claim 2 wherein the 1,3-diacyloxy-1,1,3,3-tetra(hydrocarbyl)distannoxane product is subjected to the additional step of reaction with alcoholic alkali to produce thereby a 1,3-dialkyloxy-1,1,3,3-tetra(hydrocarbyl)distannoxane.

26. Process of claim 12 wherein the 1,3-diacyloxy-1,1,3,3-tetra(alkyl)distannoxane product is subjected to the additional step of reaction with alcoholic alkali to produce thereby a 1,3-dialkyloxy-1,1,3,3-tetra(alkyl)distannoxane.

27. Process of claim 1 wherein the 1,3-diacyloxy-1,1,3,3-tetra(hydrocarbyl)distannoxane product is subjected to the additional step of reaction with aqueous alkali to produce thereby a di(hydrocarbyl)tin oxide.

28. Process of claim 2 wherein the 1,3-diacyloxy-1,1,3,3-tetra(hydrocarbyl)distannoxane product is subjected to the additional step of reaction with aqueous alkali to produce thereby a di(hydrocarbyl)tin oxide.

29. Process of claim 11 wherein the 1,3-diacyloxy-1,1,3,3-tetra(alkyl)distannoxane product is subjected to the additional step of reaction with aqueous alkali to produce thereby a dialkyltin oxide.

30. Process of claim 12 wherein the 1,3-diacyloxy-1,1,3,3-tetra(alkyl)distannoxane product is subjected to the additional step of reaction with aqueous alkali to produce thereby a dialkyltin oxide.

* * * * *